(12) United States Patent
Wada et al.

(10) Patent No.: US 6,765,124 B2
(45) Date of Patent: Jul. 20, 2004

(54) ABSORBENT ARTICLE HAVING A DEODORIZING EFFECT ON A SURFACE THEREOF

(75) Inventors: Mitsuhiro Wada, Kagawa (JP); Jun Kudo, Kagawa (JP); Hideki Kondo, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 137 days.

(21) Appl. No.: 10/162,939

(22) Filed: Jun. 4, 2002

(65) Prior Publication Data

US 2002/0188267 A1 Dec. 12, 2002

(30) Foreign Application Priority Data

Jun. 8, 2001 (JP) ........................................ 2001-174771
Jul. 12, 2001 (JP) ........................................ 2001-212900

(51) Int. Cl.⁷ ............................................... A61F 13/15
(52) U.S. Cl. ..................................... 604/359; 604/367
(58) Field of Search ................................. 604/359, 367

(56) References Cited

U.S. PATENT DOCUMENTS

| | | | |
|---|---|---|---|
| 4,356,190 A | | 10/1982 | Kraskin ........................ 424/319 |
| 6,469,227 B1 | * | 10/2002 | Cooke et al. .................. 602/48 |
| 6,517,848 B1 | * | 2/2003 | Huard et al. ................. 424/402 |
| 6,534,074 B2 | * | 3/2003 | Krzysik et al. ............... 424/402 |
| 6,603,053 B2 | * | 8/2003 | Hisanaka ...................... 604/367 |
| 6,657,100 B1 | * | 12/2003 | Underhill et al. ............ 604/361 |
| 6,689,932 B2 | * | 2/2004 | Kruchoski et al. ........... 604/360 |
| 2001/0041878 A1 | * | 11/2001 | Hisanaka ................ 604/385.01 |
| 2002/0010447 A1 | * | 1/2002 | Williams et al. ............. 604/359 |
| 2002/0128621 A1 | * | 9/2002 | Kruchoski et al. ...... 604/385.01 |
| 2002/0136755 A1 | * | 9/2002 | Tyrrell et al. ................ 424/443 |

FOREIGN PATENT DOCUMENTS

| | | | | |
|---|---|---|---|---|
| EP | 0850623 | | 7/1998 | ........... A61F/13/15 |
| JP | 8-224270 | | 9/1996 | ........... A61F/13/15 |
| JP | 9-271484 | | 10/1997 | ............. A61F/5/44 |
| JP | 410037070 A | * | 2/1998 | .......... D06M/13/10 |
| JP | 2000060908 | | 2/2000 | ............. A61G/7/05 |
| WO | WO95/24173 | | 9/1995 | ........... A61F/13/15 |

\* cited by examiner

*Primary Examiner*—John J. Calvert
*Assistant Examiner*—Michael G. Bogart
(74) *Attorney, Agent, or Firm*—Darby & Darby

(57) ABSTRACT

An absorbent article is capable of satisfactorily achieving deodorant effect or alternation restricting effect for body waste deposited on a surface sheet even in a thin absorbent sheet which can retain the body waste on the surface sheet. The absorbent article has a liquid absorbent surface sheet formed from at least one of natural fibers, regenerated fibers, mixture of natural fibers and regenerated fibers, composite fibers consisted of synthetic fiber and one of the natural fibers and the regenerated fibers, the surface sheet containing at least one of tea leaves and extract of tea leaves; and a hydrophobic back surface sheet.

21 Claims, 2 Drawing Sheets

ABSORBENT ARTICLE HAVING A DEODORIZING EFFECT ON A SURFACE THEREOF

BACKGROUND OF THE INVENTION

1. Field of the Invention

The present invention relates generally to a thin absorbent article to be used as a vaginal discharge absorptive sheet called as panty liner, a bladder control pad or urine absorptive sheet for Urinary incontinence patient, and so forth. More particularly, the invention relates to an absorbent article which can achieve deodorant effect on a surface thereof upon absorbing a body fluid or restriction effect of alternation of the body fluid.

2. Description of the Related Art

Absorbent articles having deodorant effect have been disclosed in Japanese Unexamined Patent Publication No. Heisei 8(1996)-224270 and Japanese Unexamined Patent Publication No. Heisei 9(1997)-271484. These employ leaves of green tea or catechin extracted from tea leaves as deodorant component.

In Japanese Unexamined Patent Publication No. Heisei 8(1996)-224270 as the first prior art, there has been disclosed a sanitary wearing article containing tea leaves in an absorbent body thereof. There has also been disclosed to contain the tea leaves in a surface sheet formed with a water permeable non-woven fabric.

On the other hand, in Japanese Unexamined Patent Publication No. Heisei 9(1997)-271484 as the second prior art, there has been disclosed a disposable diaper deposited epigallocatechin gallate.

However, the sanitary wearing article disclosed in the first prior art is basically directed to deodorant effect for fluid, such as menstrual blood or the like absorbed in an absorbent layer by containing tea leaves in the absorbent layer. On the other hand, in the first prior art, there is also disclosed to contain the tea leaves in the surface sheet. However, the surface sheet in the disclosed prior art is formed with a mesh form water permeable non-woven fabric to cause difficulty in retaining the tea leaves.

On the other hand, in the second prior art, there has been disclosed the invention wherein the disposable diaper is dipped in a solution of epigallocatechin gallate and is then dried. This is also to contain epigallocatechin gallate in relatively voluminous absorbent layer of the disposable diaper.

While technical concepts to contain tea leaves or extract of tea leaves in the absorbent article for deodorant effect conventionally are conventionally present, those are mainly intended to contain the tea leaves or extract of the tea leaves in the absorbent layer and are not intended to contain the tea leaves or extract of the tea leaves in the surface sheet which is in direct contact with the wearer's skin. Furthermore, there is no disclosure for particular solution for certainly holding the tea leaves or extract of the tea leaves with preventing dropout thereof when the tea leaves or extract of the tea leaves is contained in the surface sheet.

As a typical thin absorbent article, there is a vaginal discharge absorbent sheet called as panty liner. Such vaginal discharge absorbent sheet is thin and designed to be fixedly secured on the crotch part of the underwear for providing a feeling of use as if an integrated part of the underwear. The vaginal discharge absorbent sheet is thin and is not required to have large absorbing capacity. Therefore, the secrete is potentially retained on the surface of the surface sheet for a long period. Similarly, in case of a thin absorbent sheet for urinary incontinence, the urine can be retained on the surface of the surface sheet.

However, in these thin absorbent sheet, even when the tea leaves or extract of the tea leaves is held in thin absorbent layer placed inside, it should be difficult to achieve deodorant effect or alternation restricting effect for vaginal discharge, urine or the like deposited on the surface sheet.

SUMMARY OF THE INVENTION

The present invention has been worked out in view of the problems set forth above. It is an object to provide an absorbent article which can satisfactorily achieve deodorant effect or alternation restricting effect for body waste deposited on a surface sheet even in a thin absorbent sheet which can retain the body waste on the surface sheet thereof.

According to the first aspect of the present invention, an absorbent article comprises:

a liquid absorbent surface sheet formed from at least one of natural fibers, regenerated fibers, mixture of natural fibers and regenerated fibers, composite fibers consisted of synthetic fiber and one of the natural fibers and the regenerated fibers, the surface sheet containing at least one of tea leaves and extract of tea leaves; and a hydrophobic back surface sheet.

In the absorbent article, since the surface sheet contains at least one of natural fibers and regenerated fibers, the tea leaves or the extract of the tea leaves can be adhered on the natural fibers or the regenerated fibers by physical bonding force, such as intermolecular attraction, Coulomb force, hydrogen bonding force and so forth to hardly dropout. Therefore, deodorant effect and alternation restricting effect can be effected for the secrete or body waste adhering on the surface sheet.

The surface sheet may contain cotton fibers, and at least one of tea leaves and extract of tea leaves may be retained on the cotton fibers.

Since the tea leaves and/or the extract of the tea leaves can be adhered on the cotton fibers by hydrogen bonding force. On the other hand, the cotton fibers are in fibril form, so that the tea leaves and/or the extracted of the tea leaves can be held between the fibers. Therefore, the tea leaves or the extract of the tea leaves can be certainly held on the surface sheet.

The surface sheet may be consisted of a surface side non-woven fabric and a back surface side non-woven fabric laminated with each other, the surface side non-woven fabric may be formed from fibers containing the cotton fibers, and at least one of tea leaves and extract of tea leaves are retained on the cotton fibers.

By forming the surface sheet with two non-woven fabrics, absorbing performance of the secrete or body waste of the surface sheet becomes high, so that it becomes unnecessary to provide the absorbent layer below the surface sheet. Alternatively, even when the absorbent layer is provided, the absorbent layer can be thin to form the thin absorbent article. Also, by holding the tea leaves or the extract of the tea leaves on the surface side non-woven fabric of the surface sheet, deodorant effect and alternation restricting effect for secrete or body waste to be absorbed and deposed on a surface portion of the surface sheet can be effected.

The extract of tea leaves is catechins. The surface sheet may contain a coloring agent. A color of a surface of the surface sheet containing at least one of tea leaves and extract of tea leaves as well as the coloring agent may be selected among 10Y to 5B in color circle as defined in Figure 1 of Section 3.1 of JIS Z8721-1993, as viewed the color circle in clockwise direction.

By providing the foregoing color on the surface of the surface sheet, variation of color of the sheet due to containing of the tea leaves or the extract of the tea leaves becomes not perceptive but can provide visual image causing association of deodorant and bactericidal effects by the tea leaves or the extract of the tea leaves. Furthermore, the color provided on the surface of the surface sheet may be effective for concealing color due to alternation of vaginal discharge or color of urine.

A liquid absorbing region may be formed only from the surface sheet and the back surface sheet.

Since the surface sheet is effective for absorbing liquid and retaining the liquid in the absorbent article according to the present invention. Furthermore, deodorant effect and alternation restricting effect for secrete or body waste absorbed in the surface sheet can be achieved by the surface sheet. Therefore, the thin absorbent article can be formed without providing the absorbent layer.

Alternatively, the absorbent article may further comprise a cushion layer disposed between the surface sheet and the back surface sheet, and the cushion layer has hydrophobic or water repellent property.

When the cushion layer is provided, soft feeling may be provided as contacting with the wearer's skin. Furthermore, since secrete or body waste can be absorbed mainly or exclusively by the surface sheet to be influenced by the tea leaves and the like contained in the sheet to achieve deodorant effect or alternation restricting effect.

According to the second aspect of the present invention, an absorbent article comprises:
 a surface sheet formed from hydrophilic fibers fibrillated for fixedly holding powder state catechine containing substance; and
 a hydrophobic back surface sheet laminated with the surface sheet.

According to the third aspect of the present invention, an absorbent article comprises:
 a surface sheet formed from hydrophilic fibers containing fibrillated fibers for fixedly holding powder state catechine containing substance; and
 a hydrophobic back surface sheet laminated with the surface sheet.

The surface sheet may contain cotton fibers as the fibrillated fibers. The catechin containing substance may be at least one of tea leaves and extract of tea leaves.

The surface sheet may be consisted of a plurality of mutually distinct hydrophilic fiber sheets and fibers forming outermost sheet may be fibrillated for fixedly retaining the powder state catechin containing substance.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of an absorbent article according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure is not shown in detail in order to avoid unnecessary obscurity of the present invention.

Figure 1:
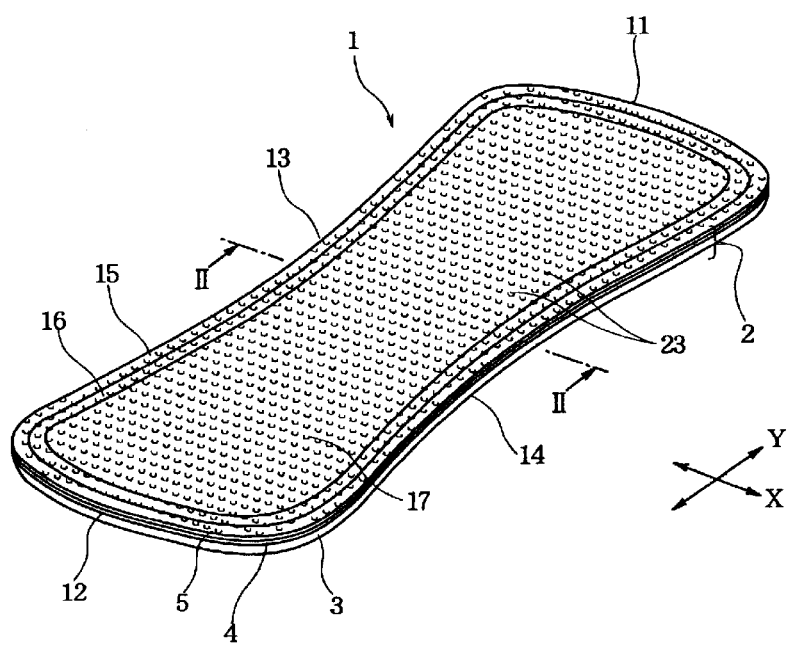
FIG. 1 is a perspective view of an absorbent article of the present invention.
Figure 2:
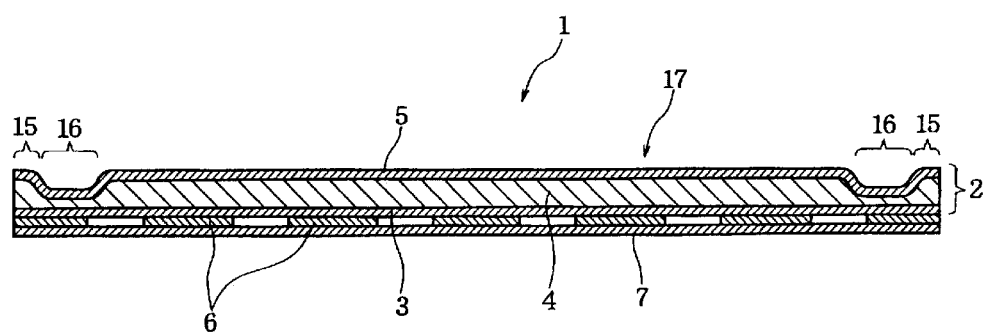
FIG. 2 is a section taken along line II—II of the absorbent article shown in FIG. 1.
Figure 3:
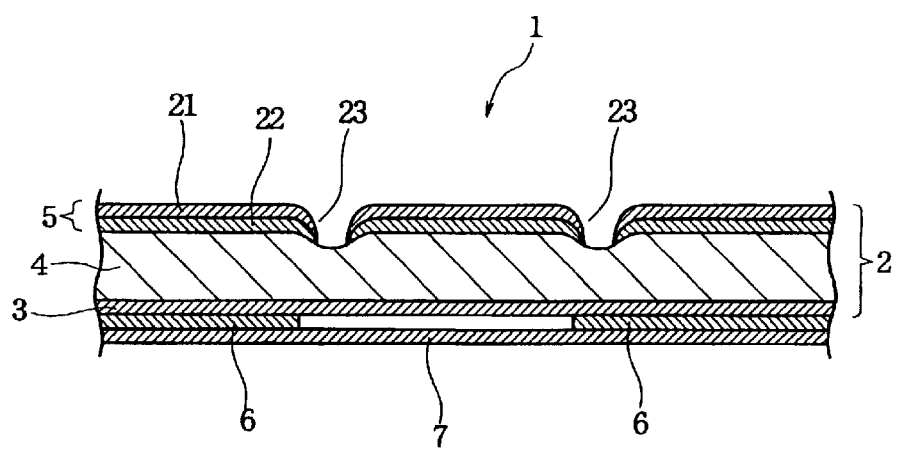
FIG. 3 is a partial enlarged view of the section shown in FIG. 2.

FIG. 1 is a perspective view of a vaginal discharge absorbent sheet called as a panty liner as one embodiment of a thin absorbent article according to the present invention (hereinafter referred to as "absorbent sheet 1"), FIG. 2 is a partial section taken along line II—II of FIG. 1, and FIG. 3 is a partial enlarged section of the section shown in FIG. 2.

Here, the vaginal discharge absorbent sheet 1 is a thin absorbent article to be used in a form integrally fixed on an inner surface of a crotch portion of an underwear for a woman in order to absorb secretion, such as vaginal discharge, to be secreted by woman. On the other hand, the thin absorbent article of the present invention can also be used for absorbing small amount of urine upon urinary incontinence by fixing on the inner surface of the crotch portion of the woman's underwear.

A main body portion 2 of the absorbent sheet 1 is formed with a laminated body of three layers consisted of a back surface sheet 3, a cushion layer 4 placed on the back surface sheet 3 and a surface sheet 5 placed on the cushion layer 4.

As shown in FIGS. 2 and 3, on the outer surface of the back surface sheet 3, a pressure sensitive adhesive layer 6 is provided for fixing the absorbent sheet on the underwear. The pressure sensitive adhesive layer 6 is formed into straight stripe form in spaced apart relationship in width direction (X direction) and extending in longitudinal direction (Y direction). The outer surface of the pressure sensitive adhesive layer 6 is covered by a releasing sheet 7.

The back surface sheet 3, the cushion layer 4, the surface sheet 5 and the releasing sheet 7 are all formed into the same plane shape. The back surface sheet 3, the cushion layer 4, the surface sheet 5 and the releasing sheet 7 are trimmed after laminating all together to form into the plane shape shown in FIG. 1.

As shown in FIG. 1, the absorbent sheet 1 is substantially sand glass shape with convex curved shape end edge portions 11 and 12 directed to abdominal part and hip part of the wearer, and concave curved shape side edge portions 13 and 14 extending in longitudinal direction. A region on inside of the seal portion 16 serves as a liquid absorbing region 17.

As shown in FIG. 2, the absorbent sheet has an outer circumference portion 15 of a predetermined width on inside of a perimeter consisted of the end edge portions 11 and 12 and the side edge portions 13 and 14, and is provided with a seal portion 16 of a predetermined width on the inner side of the outer circumference portion 15.

As shown in FIG. 3 in enlarged form, the surface sheet 5 has a structure, in which a surface side non-woven fabric 21 and a back surface side non-woven fabric 22 are laminated with each other. The surface side non-woven fabric 21 and the back surface side non-woven fabric 22 are separately formed with each other. These two non-woven fabrics 21 and 22 are formed with a large number of pores 23 in laminated condition. The pores 23 are formed by supplying the laminated non-woven fabrics 21, 22 between heated thermal emboss rolls and by piercing the laminated non-woven fabrics by means of projections on the emboss roll.

In the alternative, it is also possible to join the surface side non-woven fabric 21 and the back surface side non-woven fabric 22 by heating and pressurizing the peripheral portion by emboss rolls, and subsequently formed the pores 23 by the thermal emboss roll.

The surface side non-woven fabric 21 is a spunlaced non-woven fabric of 100% cotton fiber as natural fiber. Namely, the surface side non-woven fabric is formed by applying water jet to a dry laid or wet laid fibrous web formed from cotton fiber for entangling fibers. On the other hand, the back surface side non-woven fabric 22 is a spunlaced non-woven fabric of 100% rayon as reproduced cellulose fiber. The back surface side non-woven fabric is also formed by applying water jet to a dry laid or wet laid fibrous web for entangling fibers.

A basis weight of the surface side non-woven fabric 21 is in a range of 10 to 50 $g/m^2$, and 30 $g/m^2$ in the shown embodiment. On the other hand, the basis weight of the back surface side non-woven fabric 22 is in a range of 25 to 65 $g/m^2$, and 45 $g/m^2$ in the shown embodiment. In the surface sheet 5, the basis weight of the back surface side non-woven fabric 22 is greater than that of the surface side non-woven fabric 21. A ratio of the basis weight of the back surface side non-woven fabric 22 versus the basis weight of the surface side non-woven fabric 21 is 1.1 to 2.

Then, tea leaves such as green tea leaves or extract of the tea leaves such as green tea leaves, or mixture of both are contained in the surface side non-woven fabric 21. The extract of the tea leaves is catechins extracted from the green tea leaves, for example. Catechins is one kind of polyphenol and includes epicatechin, epicatechin gallate, epigallocatechin, epigallocatechin gallate, catechin gallate, gallocatechin gallate and the like. The extract of the tea leaves contained in the surface side non-woven fabric 21 is one or more of catechins or mixture thereof.

For example, the extract of the tea leaves in the preferred embodiment contains 31.5 Wt % of epigallocatechin gallate, 17.2 Wt % of epigallocatechin, 17.2 Wt % of gallocatechin, 5.9 Wt % of Epicatechin, 5.0 Wt % of epicatechin gallate, 2.8 Wt % of catechin gallate and 1.9 Wt % of gallocatechin gallate. Among these, epigallocatechin gallate has the highest activeness to exhibit the highest deodorant effect and bactericidal effect. Therefore, it is preferred that the extract of the tea leaves contain epigallocatechin gallate in a content greater than or equal to 25 Wt %, and preferably greater than or equal to 30 Wt %.

The extract may be extracted from the tea leaves by water, hot water and so forth and contains catechin. However, process of extraction of the extract from the tea leaves, form of the extract and grain or particle size thereof may be variable in any way as long as deemed appropriate.

The tea leaves are present in the surface side non-woven fabric 21 in a form of powder, granular, particle or particulate (hereafter generally referred to "powder"). Also, the extract of the tea leaves is present in the surface side non-woven fabric 21 in a form of powder, granular, particle or particulate (hereafter generally referred to "powder"). The tea leaves and/or the extract of the tea leaves may preferable have grain or particle size less than 2 $\mu$m.

In the surface side non-woven fabric 21, no binder is provided for fixing the tea leaves or the extract of the tea leaves. The tea leaves or the extract of the tea leaves is fixed on the cotton fibers mainly by physical bonding force. Here, the physical bonding force may be intermolecular attraction between the tea leaves or the extract of the tea leaves and the cotton fibers, Coulomb's force, hydrogen bonding force by OH radical on the surface of the cotton fibers, and holding force for the tea leaves or the extract of the tea leaves between fibrillated cotton fibers.

Then, owing to modified cross-section and amorphous structure between microfibril of cotton fibers, the powder, granular, particle or particulate state tea leaves or the extract thereof can be sucked or absorbed to be firmly boded by physical boding force.

By such physical bonding force, particularly by entangling of fibrillated cotton fibers, the tea leaves or the extract of the tea leaves can be retained within the entangled fibers to hardly cause dropout of the tea leaves or the extract of the tea leaves from the surface side non-woven fabric 21. Furthermore, since no binder is used, texture or softness of the surface of the surface side non-woven fabric 21 will not be degraded.

Alternatively, powder or microcapsule of porous material such as zeolite, amorphous carbon, silica may be employed as means for fixing the tea leaves or the extract of the tea leaves in the surface side non-woven fabric 21, for fixing the tea leaves or the extract of the tea leaves on the fibers.

In the surface side non-woven fabric 21, a coloring agent is contained together with the tea leaves and the extract of the tea leaves for coloring the surface side non-woven fabric 21. A dye to be easily dissolved in water may be employed as the coloring agent so that the surface side non-woven fabric may be easily colored by dipping the surface side non-woven fabric 21 into a solution of the coloring agent and then drying. In the alternative, a water insoluble pigment or color element is mixed with water. Then, the surface side non-woven fabric 21 is dipped into the mixture solution and then dried to fix the pigment or color element on the surface of the fiber. In the further alternative, the surface of the surface side non-woven fabric 21 can be colored by gravure or flexo printing method.

As the coloring agent, those having high security as used for medical products, foodstuff and so forth, such as chrolophyl type coloring agent originated from natural substance, such as sodium copper chlorophyllin, sodium iron chlorophyllin and so forth, may be preferably employed. Alternatively, it is possible to employ a phthalocyanine type pigment such as copper phthalocyanine blue or copper phthalocyanine green and so forth, which is water insoluble and difficult to react with catechin.

Among potential dyes and pigments to be used as coloring agent, pigment not chemically reactive to catechin is preferred. More particularly, the pigment which is free from oxidation-reduction of polyphenol containing catechin, is preferred so as to color the surface of the surface sheet without causing degradation or alternation of catechin.

In practice, the tea leaves and/or the extract of the tea leaves are applied to the cotton spunlaced non-woven fabric as the surface sheet and fixed thereon through the following process by use of a pad dryer type dyeing machine ("Z-type Heavy Duty Pad Dryer" manufactured by Tsujii Dyeing Machine Manufacturing Co., Ltd, for example). At first, a vat portion of the pad dryer type dyeing machine is filled with the solution containing the tea leaves and/or the extract of the tea leaves, the pigment and nonion-anion type surface active agent as dispersing agent. Then, the cotton spunlaced non-woven fabric is dipped into the solution, followed by dehydrating between rollers of the machine and drying by air blasting for deposition of catechins and the pigment on fibers of the surface sheet. In alternative, a drum type dyeing machine may be used in place of the pad dryer type dyeing machine.

As a color tone of the surface side non-woven fabric 21 containing the tea leaves or the extract of the tea leaves and the coloring agent, it is preferred to conceal secrete, such as vaginal discharge (achroma to light brown) or urine (light yellow) and to visually express containment of catechins. The color of the surface of the surface side non-woven fabric 21 is preferably any one of blue type, green type, yellow type or intermediate color therebetween. Particularly, the preferred color may be between 10Y to 5B as viewed in clockwise direction of a color circle of Figure 1 in Section 3.1 of JIS Z8721-1993, more preferably between 10Y to 10G, and further preferably between 10Y to 10GY (Please note that "Munsell color system" is adopted in "JIS Z8721").

The color hue of the surface of the surface side non-woven fabric 21 can be more particularly expressed by measuring with a color difference meter. For example, the color hue may be measured by a color difference meter "CR-300" manufactured by Minolta K.K. In summary of measuring method using such color difference meter, a measuring opening portion of a measuring head is abutted on a white calibration plate associated with the color difference meter to perform calibration. After calibration, the measuring opening portion is urged onto the surface side non-woven fabric as sample. Then, a measuring button is depressed. After measurement, the measured data of the sample is checked on a display portion. On the display portion, the color hue, brightness of color and chroma saturation are displayed respectively. The preferred color hue of the surface of the surface side non-woven fabric 21 obtained by this measuring method is 2.0GY to 8.0GY.

Adhering amount of the tea leaves or the extract of the tea leaves for the surface side non-woven fabric 21 is preferably in a range of 0.005 to 0.05 Wt %, and more preferably in a range of 0.005 to 0.01 Wt %. On the other hand, by containing in a range of 0.01 to 0.1 Wt % of the coloring agent in the surface side non-woven fabric, more preferably in a range of 0.02 to 0.05 Wt %, coloring with light color can be achieved without degradation of tactile feeling of the non-woven fabric.

The cushion layer 4 is a through-air bonded non-woven fabric and is formed by fusion bonding of a core-sheath type thermoplastic composite synthetic fiber consisted of a core portion of polypropylene (PP) and a sheath portion of polyethylene (PE), by hot air. This cushion layer 4 has hydrophobic property, and preferably water repellent property by providing water repellent treatment. On the other hand, a basis weight of the cushion layer 4 is in a range of 20 to 60 g/m$^2$, and can be 40 g/m$^2$, for example. The basis weight of the cushion layer 4 is smaller than the basis weight of the overall surface sheet 5 consisted of the surface side non-woven fabric 21 and the back surface side non-woven fabric 22. The basis weight of the cushion layer 4 is in a range of 0.3 to 0.8 times of the entire surface sheet 5.

In the absorbent sheet 1, the surface sheet 5 is consisted of the surface side non-woven fabric 21 and the back surface side non-woven fabric 22 having hydrophilic property and capability of absorbing liquid. The cushion layer 4 located below the surface sheet 5 has smaller basis weight than the latter and has hydrophobic property or water repellent property. Therefore, the surface sheet 5 essentially serves as absorbent layer.

Next, the back surface sheet 3 has a liquid blocking property, and is formed from a hydrophobic or water repellent non-woven fabric. This non-woven fabric is a lamination of spunbonded non-woven fabric and meltblown non-woven fabric. Assuming that spunbonded non-woven fabric is (S) and meltblown non-woven fabric is (M), the back surface sheet 3 is formed as three-layer structure consisted of the surface side and the back surface side formed with S.M.S laminated non-woven fabric formed from PP fibers, and a center portion formed with M non-woven fabric formed from PP fibers. A basis weight of the entire back surface sheet 3 is 15 to 55 g/m$^2$. For example, a basis weight of the surface side S.M.S laminated non-woven fabric is 15 g/m$^2$, a basis weight of the central M non-woven fabric is 5 g/m$^2$, and a basis weight of the back surface side S.M.S laminated non-woven fabric is 15 g/m$^2$ so that the basis weight of the entire back surface sheet is 35 g/m$^2$.

The pressure sensitive adhesive layer 6 is a rubber type hot melt adhesive and is formed into stripe form extending in parallel relationship in longitudinal direction (Y direction). The releasing sheet 7 is formed by coating a releasing resin layer such as silicon layer, on the surface of the releasing sheet 7.

The absorbent sheet 1 shown in FIGS. 1 to 3 is fitted on the inner surface of the crotch part of the underwear by the pressure sensitive adhesive layer 6 after peeling the releasing sheet 7. The surface sheet 5 is formed with the surface side non-woven fabric 21 and the back surface side non-woven fabric 22 wherein the surface side non-woven fabric 21 is formed only from the cotton fibers and the back surface side non-woven fabric 22 is formed only from rayon fibers. Both non-woven fabrics 21 and 22 have hydrophilic property. Therefore, secrete or body waste from the wearer's body is mainly absorbed by both non-woven fabrics 21 and 22. The cushion layer 4 serves for providing cushion so as to provide soft feeling in contact with the wearer's skin. Since the cushion layer 4 has hydrophobic or water repellent property, it exhibits little liquid absorbing performance. On the other hand, the cushion layer 4 assists for liquid leakage preventing function of the back surface sheet 3.

On the other hand, on the surface of the surface sheet 5, the surface side non-woven fabric 21 formed from the cotton fibers is exposed to provide soft contact feeling to the skin. On the other hand, while the tea leaves or the extract of the tea leaves and the coloring agent are contained in the surface side non-woven fabric 21, the tea leaves, the extract of the tea leaves and the coloring agent hardly dropout from the cotton fibers to exhibit superior fixing ability.

The secrete or body waste absorbed by the surface sheet 5 is absorbed by the surface side non-woven fabric 21 and the back surface side non-woven fabric. Then, since the tea leaves and the extract of the tea leaves contained in the surface side non-woven fabric 21 exposed to the surface of the surface sheet 5 exhibits deodorant effect and bactericidal effect of the tea leaves and the extract of the tea leaves, generation of offensive odor and restriction of alternation or rotting of the body waste can be achieved. Particularly, the body waste such as vaginal discharge tends to reside on the surface side non-woven fabric 21 on the surface of the surface sheet 5. However, even when the body waste resides on the surface side non-woven fabric 21, deodorant effect and bactericidal effect of the tea leaves and the extract of the tea leaves can work effectively.

On the other hand, since the surface side non-woven fabric 21 is colored, colors of secrete and body waste absorbed in the surface side non-woven fabric 21 can be concealed. Furthermore, the colors of secrete and body waste absorbed in the back surface side non-woven fabric 22 can also be concealed.

As set forth above, in the thin absorbent sheet 1, in which the surface sheet 5 exhibits liquid absorbing performance, deodorant and bactericidal effects by the tea leaves and the extract of the tea leaves can be achieved at the surface portion thereof. Also, since the surface portion of the surface sheet is colored, satisfactory concealing effect can be achieved.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

For instance, the surface sheet 5 may be formed with three or more hydrophilic non-woven fabrics. In this case, the cotton fibers may be contained in the surface side non-woven fabric located at the outermost position, and these cotton fibers may contain the tea leaves and/or the extract of the tea leaves, and the coloring agent.

On the other hand, it is also possible to form the surface sheet 5 with a single non-woven fabric formed from cotton fibers. Then, the tea leaves and/or the extract of the tea leaves and the coloring agent can be contained in the single non-woven fabric.

Furthermore, it is also possible to form the surface sheet 5 from pulp as natural fiber, in place of the cotton fibers. It is further possible to form the surface sheet from a mixture of the cotton fibers and pulp. The pulp has also high ability of fixing the tea leaves and/or the extract of the tea leaves and the coloring agent. When the pulp beaten to form microfibril on the surface is employed, performance of holding the tea leaves and/or the extract of the tea leaves and the coloring agent can be enhanced by the microfibril.

On the other hand, the surface side non-woven fabric 21 can be formed from rayon as regenerated fibers. In the alternative, the surface side non-woven fabric 21 can also be formed from synthetic fibers provided hydrophilic treatment. In such case, the tea leaves and/or the extract of the tea leaves and the coloring agent may be mixed in the synthetic material of the synthetic fibers.

Also, the cushion layer 4 may also be provided hydrophilic treatment for providing liquid absorbing ability. Also, the cushion layer may be formed from pulp or the like to form a thin absorbent layer. In such case, it is preferred that the hydrophilic cushion layer 4 or the thin absorbent layer has smaller basis weight than that of the entire surface sheet in order to provide the thin absorbent article.

Furthermore, since the surface sheet 5 has liquid absorbing ability, the cushion layer 4 can be eliminated to form the main body portion 2 of the absorbent article only with the surface sheet 5 and the back surface sheet 3.

As set forth above, in the thin absorbent article, in which the surface sheet exhibits liquid absorbing performance, deodorant and bactericidal effects for the secrete and/or body waste depositing on the surface sheet can be achieved by the tea leaves and/or the extract of the tea leaves retained in the surface sheet. Furthermore, the present invention employs the structure and construction of the absorbent article, in which the tea leaves and the extract of the tea leaves as well as the coloring agent can be stably retained in the surface sheet. Furthermore, since the present invention requires no binder for fixing the tea leaves and/or the extract of the tea leaves on the fibers of the surface sheet, texture of the surface sheet can be maintained comfortable.

What is claimed is:

1. An absorbent article comprising:

a liquid absorbent surface sheet formed from at least one of natural fibers, regenerated fibers, mixture of natural fibers and regenerated fibers, composite fibers consisted of synthetic fiber and one of the natural fibers and the regenerated fibers: said surface sheet containing cotton fibers and at least one of tea leaves and extract of tea leaves which are retained on said cotton fibers, and consisting of a surface side non-woven fabric and a back surface side non-woven fabric laminated with each and a hydrophobic back surface sheet;

wherein said surface side non-woven fabric is formed from fibers containing the cotton fibers.

2. An absorbent article as set forth in claim 1, wherein the extract of tea leaves is catechins.

3. An absorbent article as set forth in claim 1, wherein said surface sheet contains a coloring agent.

4. An absorbent article as set forth in claim 3, wherein a color of a surface of said surface sheet containing said at least one of tea leaves and extract of tea leaves as well as said coloring agent is selected from among 10Y to 5B in a color circle as defined in Figure 1 of Section 3.1 of JIS Z8721-1993, when viewing the color circle in a clockwise rotational direction.

5. An absorbent article as set forth in claim 1, further comprising:

a cushion layer disposed between said surface sheet and said back surface sheet, and said cushion layer has hydrophobic or water repellent property.

6. An absorbent article comprising:

a liquid absorbent surface sheet formed from at least one of natural fibers, regenerated fibers, mixture of natural fibers and regenerated fibers, composite fibers consisted of synthetic fiber and one of the natural fibers and the regenerated fibers, said surface sheet containing at least one of tea leaves and extract of tea leaves; and a hydrophobic back surface sheet;

wherein a liquid absorbing region is formed only from said surface sheet and said back surface sheet.

7. An absorbent article as set forth in claim 6, wherein the extract of tea leaves is catechins.

8. An absorbent article as set forth in claim 6, wherein said surface sheet contains a coloring agent.

9. An absorbent article as set forth in claim 6, wherein a color of a surface of said surface sheet containing said at least one of tea leaves and extract of tea leaves as well as said coloring agent is selected from among 10Y to 5B in a color circle as defined in Figure 1 of Section 3.1 of JIS Z8721-1993, when viewing the color circle in a clockwise rotational direction.

10. An absorbent article comprising:

a surface sheet formed from hydrophilic fibers containing fibrillated fibers for fixedly holding powder state catechine containing substance; and a hydrophobic back surface sheet laminated with said surface sheet;

wherein said surface sheet consists of a plurality of mutually distinct hydrophilic fiber sheets, and fibers forming an outermost sheet are fibrillated for fixedly retaining said powder state catechine containing substance.

11. An absorbent article as set forth in claim 10, wherein said surface sheet contains cotton fibers as said fibrillated fibers.

12. An absorbent article as set forth in claim 10, wherein said catechine containing substance is at least one of tea leaves and extract of tea leaves.

13. An absorbent article as set forth in claim 10, wherein said surface sheet contains a coloring agent.

14. An absorbent article as set forth in claim 13, wherein a color of a surface of said surface sheet containing said at least one of tea leaves and extract of tea leaves as well as coloring agent is selected from among 10Y to 5B in a color circle as defined in Figure 1 of Section 3.1 of JIS Z8721-1993, when viewing the color circle in a clockwise rotational direction.

15. An absorbent article comprising:
a surface sheet formed from hydrophilic fibers containing fibrillated fibers for fixedly holding powder state catechine containing substance; and
a hydrophobic back surface sheet laminated with said surface sheet;
wherein a liquid absorbing region is formed only from said surface sheet and said back surface sheet.

16. An absorbent article as set forth in claim 10, further comprising:
a cushion layer disposed between said surface sheet and said back surface sheet, and said cushion layer has hydrophobic or water repellent property.

17. An absorbent article as set forth in claim 15, wherein said surface sheet contains cotton fibers as said fibrillated fibers.

18. An absorbent article as set forth in claim 15, wherein said catechine containing substance is at least one of tea leaves and extract of tea leaves.

19. An absorbent article as set forth in claim 15, wherein said surface sheet consists of a plurality of mutually distinct hydrophilic fiber sheets, and fibers forming an outermost sheet are fibrillated for fixedly retaining said powder state catechine containing substance.

20. An absorbent article as set forth in claim 15, wherein said surface sheet contains a coloring agent.

21. An absorbent article as set forth in claim 20, wherein a color of a surface of said surface sheet containing said at least one of tea leaves and extract of tea leaves as well as coloring agent is selected from among 10Y to 5B in a color circle as defined in Figure 1 of Section 3.1 of JIS Z8721-1993, when viewing the color circle in a clockwise rotational direction.

* * * * *